(12) United States Patent
Theilacker-Beck et al.

(10) Patent No.: US 9,435,478 B2
(45) Date of Patent: *Sep. 6, 2016

(54) FLUID WARMER AND METHOD OF OPERATING A FLUID WARMER

(71) Applicant: WWT Technischer Geraetebau GmbH, Stuttgart (DE)

(72) Inventors: Wolfgang Theilacker-Beck, Stuttgart (DE); Matthias Theilacker, Stuttgart (DE); Klaus Schmider, Stuttgart (DE)

(73) Assignee: WWT Technischer Geraetebau GmbH, Stuttgart (DE)

( * ) Notice: Subject to any disclaimer, the term of this patent is extended or adjusted under 35 U.S.C. 154(b) by 480 days.

This patent is subject to a terminal disclaimer.

(21) Appl. No.: 13/965,252

(22) Filed: Aug. 13, 2013

(65) Prior Publication Data
US 2014/0050463 A1 Feb. 20, 2014

(30) Foreign Application Priority Data

Aug. 20, 2012 (EP) .................................... 12180968

(51) Int. Cl.
| | | |
|---|---|---|
| *F24H 1/10* | (2006.01) | |
| *A61F 7/00* | (2006.01) | |
| *F16L 53/00* | (2006.01) | |
| *A61M 5/44* | (2006.01) | |
| *H05B 1/02* | (2006.01) | |

(52) U.S. Cl.
CPC ............. *F16L 53/008* (2013.01); *A61M 5/44* (2013.01); *H05B 1/025* (2013.01)

(58) Field of Classification Search
None
See application file for complete search history.

(56) References Cited

U.S. PATENT DOCUMENTS

| | | | |
|---|---|---|---|
| 5,408,576 A * | 4/1995 | Bishop | A61M 5/445 219/386 |
| 7,403,704 B2 * | 7/2008 | Eccleston | A61F 7/12 392/466 |
| 2008/0021377 A1 * | 1/2008 | Kienman | A61M 1/1696 604/29 |
| 2012/0103958 A1 * | 5/2012 | Wallinger | H05B 3/58 219/201 |
| 2013/0072775 A1 * | 3/2013 | Rogers | A61B 5/0478 600/378 |
| 2013/0319920 A1 * | 12/2013 | Hansson | A61M 1/14 210/143 |
| 2014/0072288 A1 * | 3/2014 | Newell | A61M 5/44 392/484 |
| 2015/0094914 A1 * | 4/2015 | Abreu | B60H 1/00742 701/41 |
| 2015/0105687 A1 * | 4/2015 | Abreu | A61B 5/01 600/549 |

FOREIGN PATENT DOCUMENTS

| | | |
|---|---|---|
| DE | 10 2010 036 295 | 3/2012 |
| EP | 0 504 835 | 9/1992 |
| GB | 2 052 109 | 1/1981 |
| WO | WO 2009/105413 | 8/2009 |

* cited by examiner

*Primary Examiner* — Thor Campbell
(74) *Attorney, Agent, or Firm* — Paul Vincent (57) ABSTRACT

A fluid warmer (10) for temperature control of a medical fluid (14) guided in a fluid tube (12) and a method for operation thereof have a sensor (38), which determines a leakage current (40) via a functional grounding conductor (FE). Two supply connection conductors (22a; 22b) for a resistance heating element (18) as well as the functional grounding conductor (FE) are each equipped with a switch (30a; 30b; 30c) which can be controlled by a control device (32). The switches (30a; 30b; 30c) can be put into their open switching state jointly within a defined time interval by means of a control device (32) on occurrence of a leakage current (40) that is greater than or equal to a defined maximum threshold current magnitude ($I_{Ton}$, $I_{Toff}$).

19 Claims, 5 Drawing Sheets

FLUID WARMER AND METHOD OF OPERATING A FLUID WARMER

This application claims Paris convention priority of EP 12 180 968 filed Aug. 20, 2012 the entire disclosure of which is hereby incorporated by reference. The subject matter of this application was made by or on the behalf of parties to a joint research agreement between Stihler Electronic GmbH, Stuttgart, Germany and WWT Technischer Geraetebau GmbH, Stuttgart, Germany.

BACKGROUND OF THE INVENTION

The invention relates to a fluid warmer and a method of operating a fluid warmer.

The application of large quantities of non-warmed fluids, for example, during the intravenous administration of blood products or infusion solutions, can have disadvantageous physiological effects, one reason for this being the associated loss of body heat.

In clinical practice, fluid warmers are therefore routinely used to pre-warm the medical fluid, which flows guided in the fluid tube, to a temperature approximating the body temperature of usually 37° Celsius.

The fluid warmers according to the design that is established on the market have one or more resistance heating elements accepting alternating voltage. The resistance heating elements are provided with a first and a second power supply conductor connection for electrically conductive connection of the resistance heating element to an alternating voltage source. A heat transfer element that is thermally conductively connected to the resistance heating element is used for heat transfer to a bag-shaped vessel that is connected to a fluid tube or constituted thereby and the fluid guided in it. The heat transfer element is frequently plate-shaped to ensure efficient heat transfer to the bag-shaped vessel.

In practice, the temperature-controlled fluids come into electrically conductive contact with the person, typically bypassing the skin resistance. Resistance heating elements powered by alternating voltage, i.e., in particular line voltage of 100 V to 240 V, can, due to capacitive coupling with other components of the fluid warmer, in particular, the heat transfer element, result in disturbances of other diagnostic or therapy devices, for example, ECG units, or also of organ structures which can be electrically stimulated, in particular, the heart. The fluid warmers used in medicine must therefore always meet the high requirements for electrical safety and the strict safety standards of the international uniform classification "CF (cardiac floating)." According to these, patient leakage currents, i.e., leakage currents conducted through a person in contact with the fluid, must not exceed a current magnitude of a total of 10 µA (microamperes) under normal conditions and 50 µA in case of a fault.

It is the object of the invention to provide a fluid warmer of the above mentioned kind with a resistance heating element for alternating voltage and a method of operating such a fluid warmer that ensure a yet higher level of patient safety.

SUMMARY OF THE INVENTION

The object of the fluid warmer is achieved by a fluid warmer with the characteristics stated in the independent device claim, and the object of the method is achieved by an operating method with the characteristics stated in the independent method claim.

Further advantages and advantageous embodiments of the object of the invention result from the description, the claims, and the drawing.

In the inventive fluid warmer, the heat transfer element is functionally grounded during operation in its function as a heat transfer element. In this way, a local equipotential can be established in the region of the heat transfer element without leakage current being conducted via the person (or animal) that is in electrically conductive contact with the fluid guided in the fluid tube and vessel as so-called patient leakage currents. This can reliably counteract the danger of cardiac dysrhythmia or disturbances of other medical apparatus and devices, such as an ECG unit.

Putting the switches of the two supply connection conductors and of the functional grounding conductor into the open switching state upon detection of a leakage current that is greater than or equal to the threshold current defined (in the particular case) reliably avoids a hazard to the patient due to excessive electrical patient leakage currents, both in standalone operation of the fluid warmer and when operated in conjunction with other (medical) devices. Moreover, the complete separation of the electrically conductive connection between the resistance heating element and the alternating voltage source and simultaneous interruption of electrical conduction via the functional grounding conductor of the heat transfer element effectively prevents conduction of hazardous residual currents via the fluid warmer. The complete electrical separation of the heat transfer element from the alternating voltage source also prevents a possible flow of current via the electrical connection conductor connected to a neutral conductor of the alternating voltage source. This is the case irrespective of which of the two electrical connection conductors is connected to an energized line conductor (also called phase) and which is connected to the (de-energized) neutral conductor of the alternating current source. According to the invention, putting the switches into their open switching state can be implemented with an appropriately programmed or hardware-configured control device. To protect the patient, it is essential that the control device responds quickly on detection of an excessive leakage current, i.e. rapidly puts the switches into their open switching state. The open switching state is understood to be the switching state of the switches in which conduction of current through the switches is interrupted. The defined time interval within which the switches are put into their open switching state is always set such that a hazard to the patient due to residual or patient leakage currents can be reliably precluded.

According to the invention, different threshold currents are defined or specified for an operating condition of the fluid warmer with activated resistance heating element and for an operating condition with deactivated resistance heating element. For an activated resistance heating element, i.e. one carrying a heating current supplied by the alternating voltage source, the measurable leakage currents via the functional grounding conductor can be smaller than for a deactivated resistance heating element not carrying a heating current. This circumstance can be taken into account in practice by defining different maximum threshold currents $I_{Ton}$, $T_{Toff}$ for the two operating conditions. This can avoid unnecessary interruptions of the temperature control process due to a threshold current that is set too low for an activated resistance heating element and assure efficient temperature control of the fluid tube or of the medical fluid guided therein.

The maximum threshold current $I_{Ton}$ preferably corresponds to the sum of a current $I_{Lon}$ of the leakage current at a maximum heating power of the resistance heating element and a preferably freely defined differential current ΔI. After connection of the fluid warmer, for example, before a so-called heating mode, the magnitude of the leakage current via the functional grounding conductor can be determined, preferably at maximum heating power of the resistance heating element. For example, this can be implemented by means of an appropriately programmed or hardware-configured control device. According to the invention, the differential current can by defined by an operator or it is stored in the control device (fix). This is a simple way of taking a variable leakage current characteristic of the fluid warmer into account.

According to the invention, the differential current ΔI can be defined as a maximum threshold current $I_{Toff}$ for the leakage current in an operating condition of the fluid warmer with a deactivated resistance heating element.

According to a further embodiment of the invention, the maximum threshold current corresponds to the sum of the differential current ΔI and a current $I_{Loff}$ of the leakage current when connected to the line conductor through the switch of the supply connection conductor that is in the closed switching state and therefore energized and when a switch of the supply connection conductor of the resistance heating element connected to the neutral conductor of the alternating voltage source is simultaneously in the open (electrically non-conductive) switching state.

The differential current can have a value between 1 microampere and 50 microamperes. The differential current is preferably smaller when the fluid warmer is used simultaneously with one or more other devices on the patient than in stand-alone use of the fluid warmer.

According to a preferred further embodiment of the invention, with a current $I_L$ of the leakage current that is less than or equal to a defined minimum threshold current $I_{Lon}$, $I_{Loff}$, the switches can together be put in the open switching state by the control device within the defined time interval. According to the invention, this can, in particular, be achieved by an appropriately programmed or hardware-configured control device. In this way, patient protection can be increased still further. In standalone operation of the fluid warmer on the patient, a serious malfunction of the fluid warmer with an interrupted functional grounding conductor can be detected and the resistance heating element can be completely separated from the line supply, i.e. the alternating voltage source used to power the fluid warmer. For safety reasons, current conduction via the functional grounding conductor is thus additionally prevented by putting the switch of the functional grounding conductor into the open switching state.

According to the invention, different minimum threshold currents $I_{Ton}$, $I_{Toff}$ can be defined for the leakage current for an operating condition of the fluid warmer with an activated resistance heating element and for an operating condition with a deactivated resistance heating element. In this way, the inventive fluid warmer also provides safety advantages when operated with other electrical medical instruments/devices. For example, a drop in the leakage current conducted via the functional grounding conductor to/below the minimum threshold current can indicate a serious malfunction of the other instrument/device, in which leakage currents are largely or completely conducted via the other instrument/device. By separating an electrically conducting connection between the resistance heating element and the alternating voltage source and between the heat transfer element and the functional grounding connection in this way, electrically flowing and possibly lethal residual currents via the fluid warmer can be avoided if necessary. The minimum threshold currents are preferably smaller than the maximum currents explained above.

According to the invention, the time interval within which the switches can be put into their open switching state is preferably oriented toward the period of the alternating voltage provided by the alternating current source. The time interval is in any case shorter than a period T, preferably shorter than a half-period $T_{halb}$ of the alternating voltage (=line voltage) provided by the alternating voltage source. For example, the maximum switching time of the switches for an alternating voltage with 50 Hz is preferably less than 20 ms, preferably less than or equal to 16 ms, especially preferably less than 10 ms.

According to the invention, the controllable switches can be constituted, in particular, as electronic switches, for example, as TRIACs (bidirectional triode thyristors), or MOSFETs (metal-oxide semiconductor field-effect transistors). With electronic switches, especially short switching times can be implemented. As they have no switch contacts, wear of the switches and unwanted bouncing effects can be avoided in this way, too. In a further embodiment of the invention, the switches can also be constituted as relays. To take account of safety aspects, each switch is preferably duplicated, i.e. as two series-connected single switches each, which can be operated synchronously.

The control device can, in particular, have a visual and/or audible signaling element. In this way, on the one hand, the open switching state of the switches, i.e., active protection mode of the fluid warmer can be indicated. Malfunctions on the fluid warmer or also on other electrical devices can be immediately recognized in this way and eliminated by an operator of the fluid warmer. For easier differentiation of the trigger cause, and/or display of the normal operating mode (temperature control mode) of the fluid warmer, multiple visual/audible signaling elements can also be provided that differ by the signal they output, for example, by their color.

After switch-on of the fluid warmer and before starting temperature control, the supply connection conductor of the resistance heating element that is conductively connected to the line conductor of the alternating voltage source provided to power the fluid warmer, i.e. is energized with alternating or line voltage, can preferably be determined by the control device. According to the invention, this can be implemented, in particular, by means of an appropriately programmed or hardware-configured control device. The conducting switch of the supply connection conductor connected to the line conductor can preferably be operated individually by the control device for activation/deactivation of the resistance heating element during the temperature control process.

A still higher level of patient protection can be achieved if the fluid warmer has an electrical compensation device for compensating for the leakage current induced by operation of the resistance heating element. According to the invention, the compensation device can in particular have an electrical LC resonant circuit having an inductor L and a capacitor C that is connected to the heat transfer element. The capacitor and the inductor can be connected, in particular, in series. The inductor can, in the simplest design case, be constituted by the secondary side of a transformer T, which is electrically connected in parallel to the resistance heating element on its primary side. In this case, the primary side of the transformer is connected to the supply connection conductors of the resistance heating element and can therefore be powered from the alternating voltage source simultaneously with the resistance heating element. In this way, the LC resonant circuit can be excited to (forced) electrical oscillations having a frequency corresponding to the alternating or line voltage. Due to the phase shift of the current that this causes in the LC resonant circuit, the (capacitive) leakage current induced by the simultaneous operation of the resistance heating element can be largely compensated for. This further reduces any potential hazard to the patient. It also permits the sensor required to measure the leakage current to be implemented by means of simple instrumentation. The resonant circuit described above can also be built with electronic components (e.g. using a microprocessor).

The heat transfer element can, in particular, have a holder, for example, an insertion channel for a vessel of the fluid tube, such as a fluid bag or a fluid cartridge. This permits a large contact surface of the heat transfer element with the vessel and therefore optimum heat transfer to the fluid flowing in the vessel.

The fluid warmer can, of course, have two, three, or more resistance heating elements. The resistance heating elements can be activated or deactivated together or independently of one another for temperature control of the fluid tube/the medical fluid.

For efficient temperature control of the medical fluid, the fluid warmer preferably has a power output of at least 0.15 kilowatts, preferably of greater than 0.25 kilowatts.

The invention is explained further below using an example depicted in the drawing.

The embodiment shown and described is not to be understood as an exhaustive account but is rather an example used to describe the invention.

DESCRIPTION OF THE PREFERRED EMBODIMENT

Figure 1:
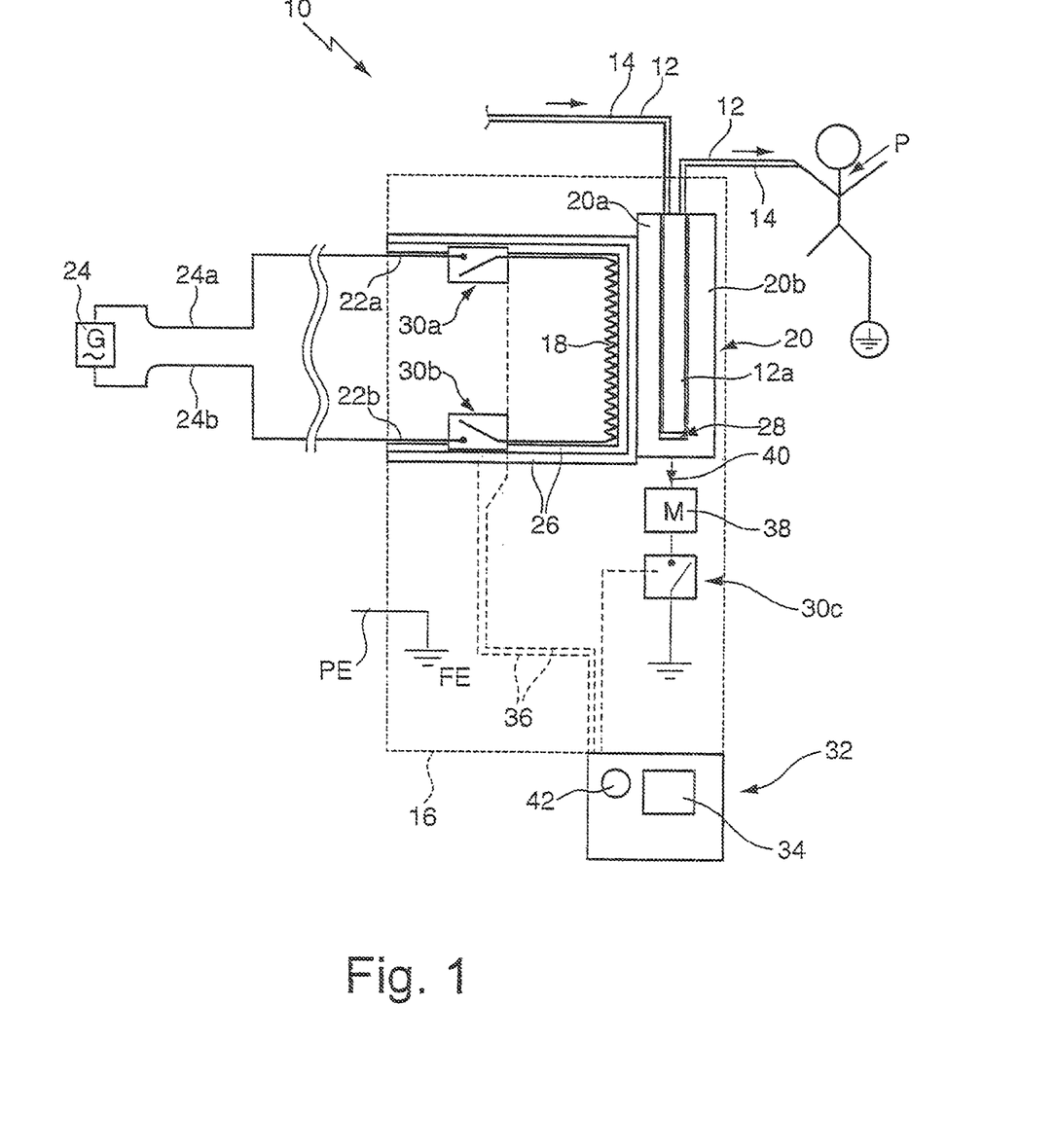
FIG. 1 a block diagram of an inventive fluid warmer with a resistance heating element accepting alternating voltage, which is thermally conductively coupled to a functionally grounded heat transfer element.

FIG. 1 shows the block diagram of a fluid warmer 10 for temperature control of a medical fluid 14 guided in a fluid tube 12. The fluid warmer 10 has a housing 16 with two or more resistance heating elements 18 disposed in the housing 16, which are thermally coupled to a heat transfer element 20, i.e., thermally conductively connected thereto. FIG. 1 shows only one of the two resistance heating elements 18. In this case, the resistance heating elements 18 are each constituted by a heating coil, but they can also have a different shape.

Each resistance heating element 18 has a first and a second supply connection conductor 22a, 22b, which are used for electrically connecting the resistance heating element 18 to a line voltage, i.e., to an external alternating voltage source 24.

The alternating voltage source 24 provided to power the resistance heating element 18 has a usual national operating voltage of, for example, 230 V+−10% and a line frequency of approximately 50 Hz.

In this case, the supply connection conductor 22a, which is the upper of the two in the Fig., of the depicted resistance heating element 18 is electrically conductively connected to a line conductor 24a of the alternating voltage source 24, while the second supply connection conductor 22b is connected to a neutral conductor 24b of the alternating voltage source 24.

The two supply connection conductors 22a, 22b and the resistance heating element 18 form a line circuit of the fluid warmer 10 that is electrically isolated from the housing 16 by means of a reinforced, here double, insulation 26.

The heat transfer element 20 is functionally grounded by means of a functional grounding conductor FE and is structured as a component that can be touched during operation. The functional grounding conductor FE is connected to the protective grounding conductor PE. The heat transfer element 20 has two heat transfer plates 20a, 20b which are disposed parallel and at a distance from each other to form a holding chamber 28. A bag-shaped expanded vessel 12a that is fluid-dynamically connected to the fluid tube 12 is pushed or laid in the holding chamber 28. The bag-shaped vessel 12a can be an integral part of the fluid tube in a known way and is essentially in contact with the two heat transfer plates 20a, 20b of the heat transfer element 20 with its full surface. This ensures optimum heat transfer to the flowing fluid 14 guided in the vessel 12a.

The fluid tube 12 is constituted by an infusion tube known in the medical sector and is made of plastic. At one end, the fluid tube is connected to the blood circulation (not shown) of a person to be treated (patient) P (via a venous access that is not depicted in any further detail/vein indwelling catheter). In this case, the fluid 14 is therefore in electrically conductive contact with the blood circulation of the person P, bypassing the usually high electrical resistance of the skin.

As shown in FIG. 1, the two supply connection conductors 22a, 22b and the functional grounding conductor FE are each provided with an electrically controllable switch 30a, 30b, 30c. The switches 30a, 30b, 30c can each be switched between a switched-on (closed) and a switched-off (open) switching state shown in the Figure. In the closed switching state, the switches 30a, 30b, 30c are conductive, i.e. their switch input is electrically connected to the switch output with low resistance. In the open switching state, the switches 30a, 30b, 30c are non-conductive, i.e., their inputs and outputs are electrically isolated from each other in the open switching state. In this case, the switches 30a, 30b, 30c are constituted by relays but can also be constituted by MOSFETs (metal-oxide-semiconductor field-effect transistors), by TRIACs (bidirectional triode thyristors), or the like.

A control device 32 with a display and operator panel 34 is used in this case as a control for all operating parameters of the fluid warmer 10. The control device 32 is connected to the switches 30a, 30b, 30c via control cables 36. The control device 32 has a sensor 38 for measuring of a leakage current 40 conducted via the function ground conductor FE.

The defined time interval within which the switches 30a, 30b, 30c can be put into their open switching state by the control device 32 is always less than one period, preferably less than one half-period, of the alternating voltage used to power the resistance heating elements 18. The time interval is in particular less than or equal to 16 ms for a line frequency of 50 Hz.

The control device 32 has a signaling element 42 to output a visual and/or audible alarm signal.

Figure 2:
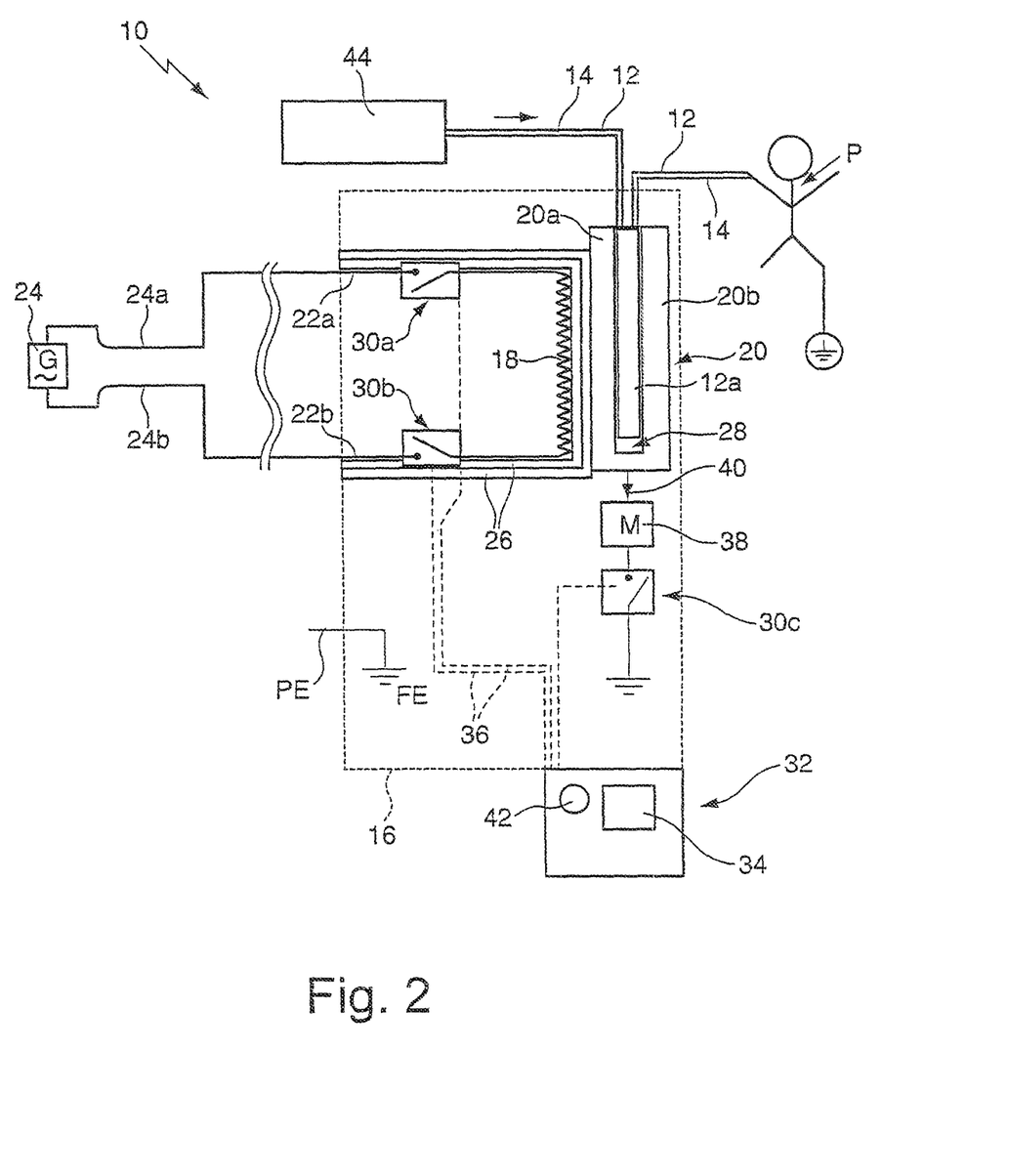
FIG. 2 the fluid warmer from FIG. 1 used jointly with a dialysis machine.

FIG. 2 shows the fluid warmer 10 in combined use with a further medical device 44, here a dialysis machine on a person P to be treated. As is known, dialysis machines are used for renal replacement therapy for removal of dissolved substances and, if necessary, a defined water component from the blood of the patient. The dialyzed blood flows from the dialysis machine, via the fluid warmer 10 in which the blood is warmed, to the person P.

Figure 3:
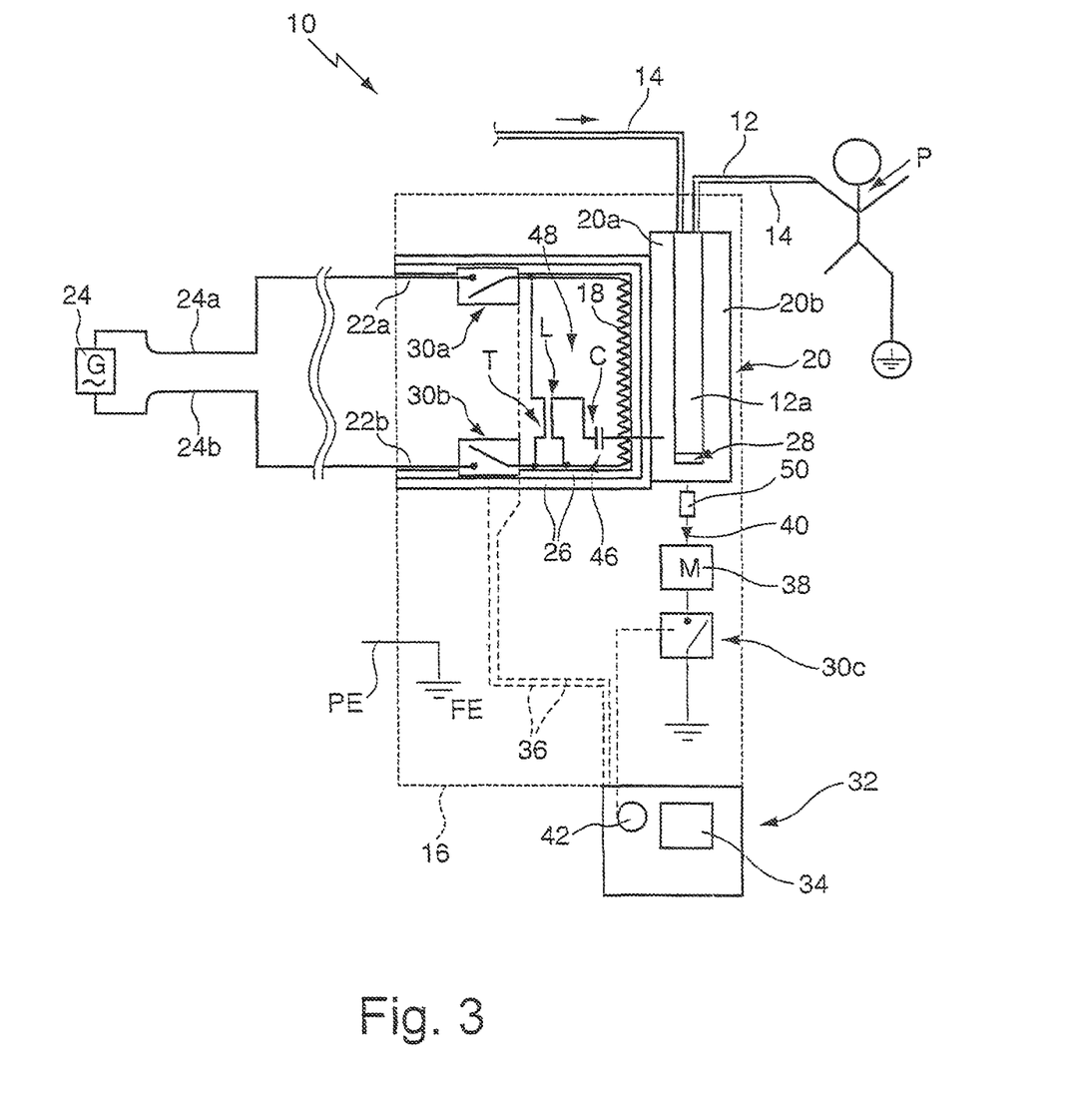
FIG. 3 a block diagram of an inventive fluid warmer that has an electrical compensation device to compensate for a leakage current induced in the heat transfer element by the resistance heating element.

FIG. 3 shows a fluid warmer 10 that, unlike the fluid warmer explained above, additionally has an electrical compensation device 46 for the leakage current 40 induced by operation of the resistance heating elements 18. The compensation device 46 has an LC resonant circuit 48 with an inductor L and a capacitor C. The LC resonant circuit 48 is connected to the heat transfer element 20 and the supply connection conductor 22b, which is connected to the neutral conductor of the alternating voltage source 24. In this case, the inductor L and the capacitor C of the LC resonant circuit 48 are connected in series. The inductor L is constituted by a secondary side of a transformer T, whose primary side is connected to the two supply connection conductors 22a, 22b. When the resistance heating elements 20 and the transformer T are jointly powered by the line voltage of the alternating voltage source 24, the LC resonant circuit 48 is excited to forced electrical oscillations. Because of a phase shift of the current in the LC resonant circuit 48 with respect to the heating current of the resistance heating elements 20, the leakage current 40 induced by the resistance heating elements is at least partially compensated for. The resonant circuit 48 described above can also be constructed with electronic components (e.g. using a microprocessor). A resistance element 50 is connected in front of the sensor 38 in this example of the fluid warmer 10.

Figure 4:
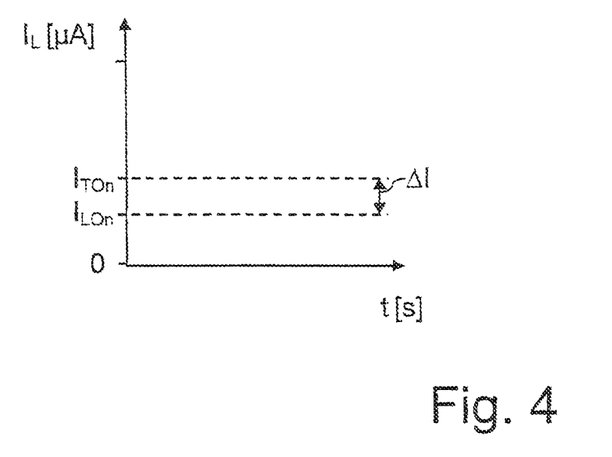
FIG. 4 threshold currents defined for regulation of the fluid warmer according to FIGS. 1 through 3 for a leakage current, which can be measured, via the functional grounding conductor of the heat transfer element with an activated resistance heating element.

FIG. 4 illustrates a maximum threshold current $I_{Ton}$ and a minimum threshold current $I_{Lon}$ for the magnitude $I_L$ of the leakage current 40, by which the switching state of the switches 30a, 30b, 30c is controlled by the control device 32 in the case of an activated resistance heating element 18 (FIGS. 1 and 2). The difference between the maximum threshold current $I_{Ton}$ and $I_{Lon}$ corresponds to a differential current $\Delta I$.

Figure 5:
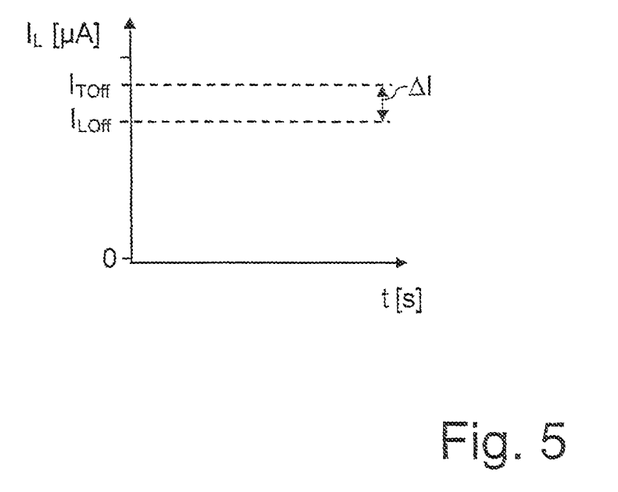
FIG. 5 threshold currents defined for regulation of the fluid warmer according to FIGS. 1 through 3 for a leakage current, which can be measured, via the functional grounding conductor with a deactivated resistance heating element.

FIG. 5 illustrates a maximum threshold current $I_{Toff}$ and a minimum threshold current $I_{Loff}$ for the magnitude $I_L$ of the leakage current 40 conducted via the functional grounding conductor FE, by which the switching state of the switches 30a, 30b, 30c is controlled by the control device 32 during temperature control in the case of a deactivated resistance heating element 18 (FIGS. 1 and 2). The difference between the maximum threshold current $I_{Toff}$ and the minimum threshold current $I_{Loff}$ corresponds to the differential current $\Delta I$. The differential current $\Delta I$ can be defined by the user.

Figure 6:
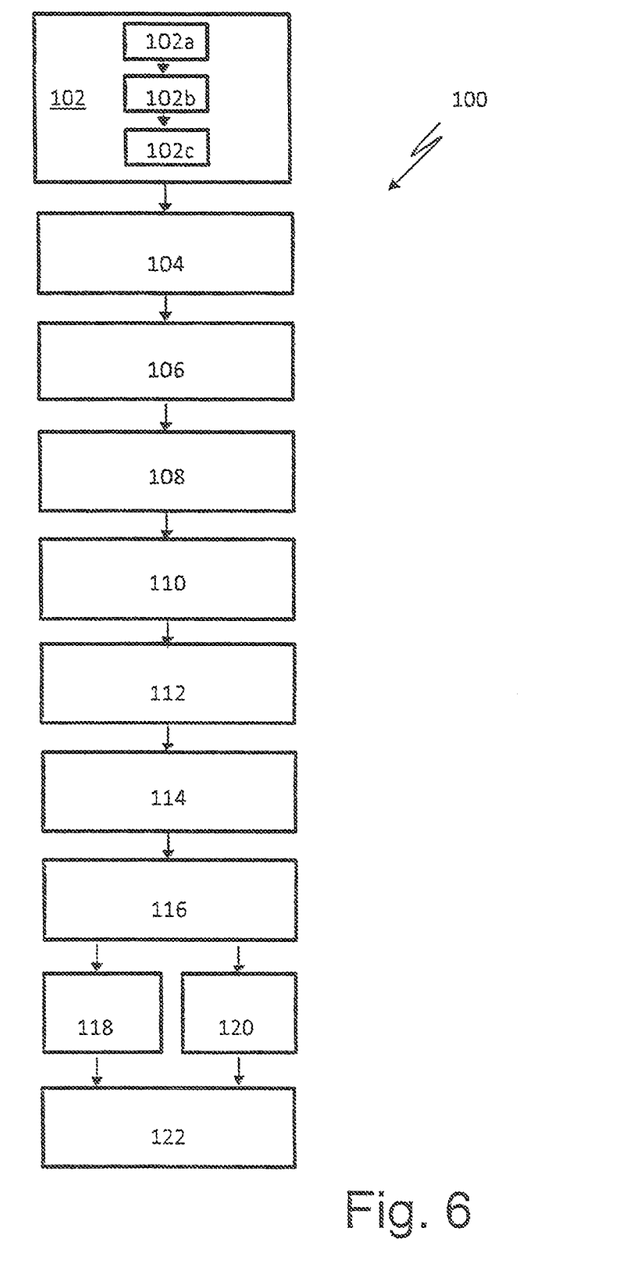
FIG. 6 a block diagram with individual steps of the inventive method of operating the fluid warmer from FIGS. 1 through 3.

The inventive method 100 of operating the fluid warmer 10 from FIGS. 1 and 2 is explained below with additional reference to FIG. 6.

In this case, the control device 32 (FIGS. 1, 2) of the fluid warmer 10 is programmed to perform the individual steps of the method. The control device can however permit the method 100 to be performed purely by its hardware configuration.

After the fluid warmer 10 has been connected to the alternating voltage source 24 and the fluid warmer 10 has been switched on, the control device 32 is initially in a standby mode.

Before the heating is started, the control device 32 identifies in a first step 102 the supply connection conductor 22a, 22b that is connected to the line connector of the alternating voltage source 24 and is therefore energized when the associated switches 30a, 30b, 30c are closed.

For this purpose, in a first sub-step 102a, the magnitude $I_{L1}$ of the leakage current 40 via the functional grounding conductor FE with switch 30a of the first supply connection conductor 22a open (here connected to the line conductor of the alternating voltage source 24) and switch 30b of the second supply connection conductor 22b closed (here connected to the neutral conductor of the alternating voltage source 24) is determined by means of the sensor 38 and stored by the control device 32.

In a second sub-step 102b, a magnitude $I_{L2}$ of the leakage current 40 via the functional grounding conductor FE with switch 30a of the first supply connection conductor 22a closed and switch 30b of the second supply connection conductor 22b open is determined by means of the sensor 38 and stored by the control device 32. Of course, switch 30c of the functional grounding conductor FE is closed in both of the above-mentioned sub-steps 102a, 102b.

In a third sub-step 102c, the supply connection conductor 22a, 22b connected to the line conductor is identified by the sensed and stored current magnitudes $I_{L1}$, $I_{L2}$. The supply connection conductor 22a, 22b connected to the line conductor is the supply connection conductor 22a, 22b in which the leakage current 40 is larger in the conductive (closed) switching state of the switch 30a, 30b assigned to the supply connection conductor 22a, 22b.

The switch 30a of the neutral conductor 22a is defined by the control device 32 in a further step 104 as a controllable switch 30a, 30b, 30c for activation/deactivation of the resistance heating element 18 during temperature control of the fluid 14.

In a further step 106, the control device 32 determines a current magnitude $I_{Lon}$ via the functional grounding conductor FE at a maximum heating power (full load) of the resistance heating element 18.

In a following step 108, the control device 32 defines the maximum threshold current $I_{Ton}$ as a sum of the current magnitude $I_{Lon}$ with an activated resistance heating element and the differential current $\Delta I$:

$$I_{Ton} = I_{Lon} + \Delta I \quad (I)$$

In a further step 110, the control device 32 defines the maximum threshold current $I_{Ton}$ defined in this way for temperature control of the fluid warmer 10 with an activated resistance heating element 18. Note that the two switches 30a, 30b of the supply connection conductors 22a, 22b are each in their closed switching state with an activated resistance heating element 18 so that the resistance heating element 18 is carrying a heating current supplied by the alternating voltage source 24.

In a further step 112, the control device 32 defines the maximum threshold current $I_{Toff}$ for the leakage current 40 conducted via the functional grounding conductor FE in an operating condition of the fluid warmer 10 with a deactivated heating element 18.

As explained above, the switch 30a of the first supply connection conductor 22a connected to the neutral conductor 24a of the alternating voltage source 24 is in its open switching state with a deactivated resistance heating element 18 and the switch 30b of the supply connection conductor 22b connected to the line conductor is in its closed switching state.

The control device defines the maximum threshold current $I_{Toff}$ as the sum of the current magnitude $I_{Loff}$ and the differential current $\Delta I$:

$$I_{Toff} = I_{Loff} + \Delta I$$

The maximum threshold current $I_{Toff}$ is defined in a further step 114 by the control device 32 for the leakage current 40 and for temperature control of the fluid warmer 10 with a deactivated heating element 18.

The differential current $\Delta I$ can be between 1 microampere and no more than 50 microamperes and can be stored in the control device 32 as a fixed value (stored). The differential current $\Delta I$ can also be changed or manually entered or defined by an operator, for example, via operator panel 34 of the control device.

Of course, with simultaneous use of the fluid warmer 10 on a patient P with one or more other devices (FIG. 2), a smaller differential current $\Delta I$ is chosen than in standalone operation of the fluid warmer 10 as illustrated in FIG. 1.

The control device 32 can monitor the leakage current 40 via the functional grounding conductor FE during temperature control in a further step 116, preferably continuously.

The control device 32 compares the leakage current 40, having an activated resistance heating element 18, with the maximum threshold current $I_{Ton}$ and, having a deactivated resistance heating element, with the maximum threshold current $I_{Toff}$. In a further step 118, as soon as the leakage current 40 reaches or exceeds the maximum threshold current $I_{Ton}$ defined for the operating condition of the fluid warmer (activated/deactivated resistance heating element 18), the control device 32 puts the switches 30a, 30b of the first and second supply connection conductors 22a, 22b and the switch 30c of the functional grounding conductor FE jointly in their open switching state within the defined time interval so that the fluid warmer 10 is in an activated protection mode.

In a further step 120, during temperature control of the fluid warmer 10, the control device 32 can also put the switches 30a, 30b, 30c jointly into their open switching state within the defined time interval on occurrence of a leakage current 40 that is less than or equal to the defined minimum threshold current $I_{Lon}$, $I_{Loff}$. In standalone operation of the fluid warmer 10, faulty functional grounding FE of the heat transfer element 20 can thus be detected and a hazard for the patient P due to undesirably high patient leakage currents can be counteracted. Furthermore, in simultaneous use of the fluid warmer 10 with a further device on the patient P, disturbances of the other device can be detected in which capacitive leakage currents are mainly or solely conducted via the other device. The fluid warmer 10 is, here too, in its activated protection mode.

The activated protection mode of the fluid warmer 10 is displayed by the signaling element 42 in a final step 122.

The invention relates to a fluid warmer 10 for temperature control of a medical fluid 14 guided in a fluid tube 12. The fluid warmer 10 comprises
- a resistance heating element 18 for alternating voltage that has a first and a second electrical supply connection conductor 22a, 22b;
- a heat transfer element 20 that is thermally conductively connected to the resistance heating element 18;
- a functional grounding conductor FE for functionally grounding the heat transfer element 20;
- a sensor 38 for determining the present magnitude of a leakage current 40 via the functional grounding conductor FE; and
- a control device, wherein the two supply connection conductors 22a, 22b and the functional grounding conductor FE are each provided with switches 30a, 30b, 30c, and wherein the switches 30a, 30b, 30c for a leakage current 40 that is greater than or equal to a defined maximum threshold current $I_{Ton}$, $I_{Toff}$ are put into their open switching state by the control device within a defined time interval.

We claim:

1. A fluid warmer for temperature control of a medical fluid guided in a fluid tube, the warmer comprising:
    a resistance heating element for alternating voltage, said resistance heating element having a first and a second electrical supply connection conductor, wherein said first electrical supply connection conductor has a first switch and said second electrical supply connection conductor has a second switch;
    a heat transfer element which is thermally coupled to said resistance heating element;
    a functional grounding conductor, which is electrically conductively connected to said heat transfer element, said functional grounding conductor having a third switch;
    a sensor for determining a present magnitude of a leakage current via said functional grounding conductor; and
    a control device, said control device being structured to simultaneously switch said first, said second and said third switches into an open switching state within a defined time interval on occurrence of a leakage current that is greater than or equal to a defined maximum threshold current magnitude.

2. The fluid warmer of claim 1, wherein different threshold current magnitudes are defined for an operating condition of the fluid warmer with an activated resistance heating element and for an operating condition with a deactivated resistance heating element.

3. The fluid warmer of claim 1, wherein the maximum threshold current magnitude corresponds to a sum of a current magnitude of leakage current for a maximum heating power of the resistance heating element and a defined differential current magnitude.

4. The fluid warmer of claim 1, wherein the maximum threshold current magnitude corresponds to a differential current magnitude or to a sum of a differential current magnitude and a current magnitude of leakage current with a closed switch of a supply connection conductor connected to a line conductor of the alternating voltage source and with an open switch of a supply connection conductor connected to a neutral conductor of the alternating voltage source.

5. The fluid warmer of claim 3, wherein said differential current is between 1 microampere and no more than 50 microamperes.

6. The fluid warmer of claim 4, wherein said differential current is between 1 microampere and no more than 50 microamperes.

7. The fluid warmer of claim 1, wherein said first, second and third switches can be put into open switching states thereof within a defined time interval on occurrence of a leakage current which is less than or equal to a defined minimum threshold current magnitude.

8. The fluid warmer of claim 7, wherein different threshold current magnitudes are defined for an operating condition of the fluid warmer with an activated resistance heating element and for an operating condition with a deactivated resistance heating element.

9. The fluid warmer of claim 1, wherein said defined time interval within which switches can be put into said open switching state by said control device is less than one period or less than one half-period of the alternating voltage used to power the resistance heating element.

10. The fluid warmer of claim 1, wherein said first, second and third switches are constituted as a bidirectional triode thyristor, as a metal-oxide semiconductor field-effect transistor, as a relay or as switches which are duplicated.

11. The fluid warmer of claim 1, wherein a supply connection conductor that is conductively connected to a line conductor of the alternating voltage source can be identified by said control device and a switch of this supply connection conductor can be controlled during operation of the fluid warmer by said control device to activate or deactivate said resistance heating element.

12. The fluid warmer of claim 1, further comprising an electrical or electronic compensation device for compensation of the leakage current induced by said resistance heating element.

13. The fluid warmer of claim 12, wherein said compensation device comprises an LC resonant circuit with an inductor and a capacitor.

14. The fluid warmer of claim 13, wherein said inductor of said LC resonant circuit is constituted as a secondary side of a transformer, whose primary side is connected to said first and said second supply connection conductors of said resistance heating element.

15. The fluid warmer of claim 1, wherein said heat transfer element has a holding chamber for a bag-shaped vessel of the fluid tube.

16. The fluid warmer of claim 1, wherein two or more resistance heating elements are provided.

17. The fluid warmer of claim 1, wherein a power output totals at least 0.15 KW or more than 0.2 KW.

18. A method for operating a fluid warmer for temperature control of a fluid flowing in a fluid tube, the fluid warmer comprising:
a resistance heating element having a first and a second electrical supply connection conductor for connecting the resistance heating element to an alternating voltage source, the first electrical supply connection conductor having a first switch and the second electrical supply connection conductor having a second switch;
a heat transfer element, which is thermally coupled to the resistance heating element for transferring heat to the fluid flowing in a vessel of the fluid tube;
a functional grounding conductor connected to the heat transfer element for functional grounding of the heat transfer element, the functional grounding conductor having a third switch;
a sensor for sensing a leakage current via the functional grounding conductor; and
a control device for controlling the first, second and third switches;
the method comprising the steps of:
a) defining a maximum threshold current magnitude for a leakage current via the functional grounding conductor;
b) comparing a leakage current measured with the sensor with the defined maximum threshold current magnitude; and
c) putting the first, second and third switches into open switching states thereof within a defined time interval on occurrence of a leakage current, which is greater than or equal to the defined maximum threshold current magnitude.

19. The method of claim 18, further comprising the steps of:
d) comparing the leakage current measured with the sensor with a defined minimum threshold current magnitude; and
e) putting the first, second and third switches into open switching states within the defined time interval on occurrence of a leakage current which is less than or equal to the minimum threshold current magnitude.

* * * * *